US008448247B2

(12) United States Patent
Stute

(10) Patent No.: US 8,448,247 B2
(45) Date of Patent: May 21, 2013

(54) ADAPTIVE BEHAVIORAL INTRUSION DETECTION SYSTEMS AND METHODS

(75) Inventor: Michael Stute, Plano, TX (US)

(73) Assignee: Global Dataguard Inc., Addison, TX (US)

( * ) Notice: Subject to any disclaimer, the term of this patent is extended or adjusted under 35 U.S.C. 154(b) by 13 days.

(21) Appl. No.: 13/453,879

(22) Filed: Apr. 23, 2012

(65) Prior Publication Data

US 2012/0210429 A1  Aug. 16, 2012

Related U.S. Application Data

(63) Continuation of application No. 10/504,731, filed as application No. PCT/US03/09543 on Mar. 28, 2003, now Pat. No. 8,205,259.

(60) Provisional application No. 60/368,628, filed on Mar. 29, 2002.

(51) Int. Cl.
*G06F 21/00* (2006.01)

(52) U.S. Cl.
USPC .............................................. 726/23; 726/24

(58) Field of Classification Search
None
See application file for complete search history.

(56) References Cited

U.S. PATENT DOCUMENTS

| 5,892,903 | A  | 4/1999  | Klaus |
| 6,279,113 | B1 | 8/2001  | Vaidya |
| 6,282,546 | B1 | 8/2001  | Gleichauf et al. |
| 6,301,668 | B1 | 10/2001 | Gleichauf |
| 6,321,338 | B1 | 11/2001 | Porras et al. |
| 6,477,651 | B1 | 11/2002 | Teal |
| 6,487,666 | B1 | 11/2002 | Shanklin et al. |
| 7,032,005 | B2 | 4/2006  | Mathon et al. |
| 7,143,442 | B2 | 11/2006 | Scarfe et al. |
| 7,215,637 | B1* | 5/2007 | Ferguson et al. .......... 370/230.1 |
| 7,307,999 | B1* | 12/2007 | Donaghey .................... 370/465 |
| 7,493,659 | B1* | 2/2009 | Wu et al. ........................ 726/26 |
| 2002/0023227 | A1 | 2/2002 | Sheymov et al. |
| 2002/0082886 | A1 | 6/2002 | Manganaris et al. |
| 2002/0083343 | A1 | 6/2002 | Crosbie et al. |

(Continued)

FOREIGN PATENT DOCUMENTS

WO    0223805 A2    3/2002

OTHER PUBLICATIONS

Lee, "A Data Mining and CIDF Based Approach for Detecting Novel and Distributed Intrusions," H. Debar, et al. editors: RAID 2000, LNCS 1907, pp. 49-65, 2000, Springer-Vertag, Berlin, Deidelberg 2000.

(Continued)

*Primary Examiner* — Michael S McNally
*Assistant Examiner* — Carlton Johnson
(74) *Attorney, Agent, or Firm* — Klemchuk Kubasta LLP; Darin M. Klemchuk

(57) ABSTRACT

Systems and methods for analyzing historical network traffic and determining which traffic does not belong in a network are disclosed. Intrusion detection is performed over a period of time, looking for behavioral patterns within networks or information systems and generating alerts when these patterns change. The intrusion detection system intelligently forms correlations between disparate sources to find traffic anomalies. Over time, behaviors are predictive, and the intrusion detection system attempts to predict outcomes, becoming proactive instead of just reactive. Intrusions occur throughout whole information systems, including both network infrastructure and application servers. By treating the information system as a whole and performing intrusion detection across it, the chances of detection are increased significantly.

20 Claims, 10 Drawing Sheets

U.S. PATENT DOCUMENTS

2002/0083344 A1 6/2002 Vairavan
2002/0133721 A1 9/2002 Adjaoute
2002/0178383 A1 11/2002 Hrabik et al.

OTHER PUBLICATIONS

Porras, et al., "Live Traffic Analysis of TCP/IP Gateways," 1998 ISOC Symposium on Network and Distributed Systems Security, pp. 1-13, Dec. 12, 1997.

Shipley and Mueller, "Dragon Claws its Way to the Top." 19 pages, Aug. 20, 2001, http://www/networkcomputing.com/1217/121712.html.

Allan, "Intrusion Detection Systems (IDSs): Perspective," pp. 1-20, Jan. 4, 2002.

Paly, "Network Security: Tracking Hacker Behavior Patters," 2 pages, Dec. 10, 2001, http://www/dfwtechbiz.com/idsplayarticledetail.asp?art_id=52874.

European Search Report in related European Patent Application No. 03719499.0.

International Search Report in related Application No. PCT/US03/09543.

Written Opinion in related Application No. PCT/US03/09543.

* cited by examiner

ADAPTIVE BEHAVIORAL INTRUSION DETECTION SYSTEMS AND METHODS

CROSS-REFERENCE TO RELATED APPLICATIONS

This application is a continuation of pending U.S. patent application Ser. No. 10/504,731, filed Aug. 16, 2004, which is the U.S. national phase of International Application No. PCT/US03/09543, filed on Mar. 28, 2003, and which further claims the benefit of U.S. Provisional Patent Application No. 60/368,629, filed Mar. 29, 2002, entitled "Adaptive Behavior Intrusion Detection Systems and Methods," the entire contents of these applications are hereby incorporated by reference.

FIELD OF THE DISCLOSURE

The present disclosure relates generally to methods and systems for providing security on a communication system and, more particularly, the disclosure relates to adaptive behavioral intrusion detection.

BACKGROUND OF THE DISCLOSURE

With the rise of the Internet and the use of computer networks by many businesses, network security has become increasingly important. The rise of e-commerce has led to organizations opening their networks to wider audiences over the Internet in order to stay competitive. Such open networks expose the organizations to intrusions—attempts to comprise the confidentiality, integrity, or availability, or to bypass the security mechanisms of a computer system or network. Additionally, companies storing vast amounts of consumer data need to provide some reasonable method for assuring privacy.

Attackers or hackers have continued to alter their attacks and network subversion methods, and vulnerabilities continue to exist in many areas including network misconfiguration, poorly engineered software, user neglect and carelessness, and basic design flaws in protocols and operating systems. Furthermore, as the sophistication of tools used by hackers has increased, the technical knowledge required to attack a network has fallen. Additionally, attacks are often the result of malicious insider activity which cannot be prevented by perimeter defenses.

Intrusion detection is the process of monitoring the events occurring in a computer system or network and analyzing them for signs of intrusion. An intrusion detection system (IDS) is a software product or hardware device that automates the intrusion detection process, and an IDS typically includes three functional components: information sources, analysis, and response. Analysis strategy falls into two basic types: knowledge-based misuse detection and behavioral-based anomaly detection. Behavioral-based detection methods use information about repetitive and usual behavior on the systems they monitor and note events that diverge from expected usage patterns.

Intrusion detection allows organizations to protect their systems from the threats that come with increasing network connectivity and reliance on information systems. Given the level and nature of modern network security threats, IDSs have gained acceptance as a necessary addition to every organization's security infrastructure. IDSs automatically review massive amounts of network and system data in real time, identify suspicious activity, provide real-time automated notification to security personnel, guide further investigation, and sometimes automatically respond to specified attacks. Properly used, an IDS can detect common attacks, attempts to exploit known weaknesses, network probes, or critical resource overloads in a reasonably timely manner. By identifying successful invalid activity, IDSs can indirectly spotlight network and system vulnerabilities, enabling fixes and fine-tuning.

Comprehensive network security requires multiple layers. An effective IDS includes both knowledge-based and behavioral-based components. Most vendors provide network security products that protect only against known or "signature" patterns of attack, and typical behavioral-based components are limited to single anomaly detection without looking for behavioral patterns over a longer period of time. Existing products ignore troublesome new behavioral patterns that have yet to be detected or documented. Hackers often follow certain behavioral patterns that double as calling cards for their personal invasive techniques. For example, a hacker may attack all of the hacker's targeted networks by a recognizable and consistent sequence of port access attempts, but the pattern is recognized as odd or alarming only after an attack has occurred and a profile for that behavior is documented and publicized. Signature and basic behavioral methods of threat detection are invaluable, but they fall short as hackers determine new ways to attack or adjust their old behavior to attract less attention.

Many serious intruders perform considerable amounts of probing work within a network to learn how it is constructed and understand its weaknesses prior to a concerted attack. This reconnaissance work is commonly recorded in automated server and network logs, but largely remains unnoticed by most network IDSs if the traffic anomaly does not fit the profiles of known or common "signature" hacks. Accordingly, there is a need for a system with adaptive technology that, over time, gathers information on a particular system and establishes a pattern of normal traffic. Such a system is able to more intelligently determine which network traffic signatures do not fit the normal profiles for the individual system and alerts an intrusion detection team for further investigation and appropriate rapid defensive action.

SUMMARY OF THE DISCLOSURE

Systems and methods for analyzing historical network traffic and determining which traffic does not belong in a network are disclosed. Intrusion detection is performed over a period of time, looking for behavioral patterns within networks or information systems and generating alerts when these patterns change. Normal traffic behavior is collected on a continuing basis to establish a baseline for comparison with future network traffic. Once a statistically significant sample of historical data has been compiled, a behavioral intrusion detection agent is activated. The intrusion detection system intelligently forms correlations between disparate sources to find traffic anomalies. Over time, behaviors are predictive, and the intrusion detection system attempts to predict outcomes, becoming proactive instead of just reactive. Intrusions occur throughout whole information systems, including both network infrastructure and application servers. By treating the information system as a whole and performing intrusion detection across it, the chances of detection are increased significantly.

An exemplary embodiment of a method according to the present disclosure for detecting network intrusion attempts associated with network objects on a communications network includes collecting normal traffic behavior associated with network objects on the network on a continuing basis to establish historical data regarding traffic across the network.

Network traffic associated with network objects on the network is monitored to detect anomalies, which are analyzed using the historical data. Alerts are generated identifying possible intrusion attempts based on analysis of the anomalies. The historical data is continually updated based on the anomalies, the alerts, and network traffic.

In an exemplary embodiment, monitoring network traffic to detect anomalies may include monitoring network traffic for known strings and series of bytes that indicate signature attacks. Monitoring network traffic may also include applying a series of rules to identify anomalous packets and adding the anomalous packets to an anomaly pool. In an exemplary embodiment, analyzing the anomalies using the historical data includes analyzing packets in the anomaly pool independently of any of the series of rules that identified the packet for addition to the anomaly pool. Analyzing the anomalies using the historical data may also include conducting a threshold analysis to determine whether a data point is within threshold values.

In an exemplary embodiment, generating alerts identifying possible intrusion attempts includes adding alerts to an alert pool and releasing alerts to a console for viewing by an operator. According to another exemplary embodiment, generating alerts may include an alert release system, where a first set of alerts are added to an alert pool, internet protocol addresses associated with each alert in the alert pool are resolved with a name and each alert in the alert pool is renamed with a name recognizable by an operator, a set of rules is applied to select alerts from the alert pool to be displayed on a console for viewing by the operator, the rules comprising high level selection parameters that have been previously defined, and the selected alerts are released by name to the console for viewing by the operator.

Certain exemplary embodiments of methods of the present disclosure may be performed across a plurality of networks and with the results compiled in a global database, and historical data may be updated based on results in the global database.

A computer storage medium storing a computer program, when executed by a computer-controlled apparatus, may cause the computer-controlled apparatus to perform certain exemplary embodiments of methods according to the present disclosure. Additionally, a computer-controlled apparatus may be operative for implementing certain exemplary embodiments of methods of the present disclosure.

In an exemplary embodiment of a system according to the present disclosure, an intrusion detection system for detecting network intrusion attempts associated with network objects on a communications network includes a sensor connected to the network for monitoring network traffic associated with network objects on the network. The sensor may include a knowledge-based component for examining network traffic for known strings and series of bytes that indicate signature attacks and a packet logger for reading packets in network traffic, classifying packets by protocols, and creating packages of compressed packets. A server connected to the sensor accepts real-time alerts for possible signature attacks, and a converter is provided for converting alerts from native signature format to a unified format for storage in at least one relational database. An analysis server receives compressed packets from the sensor at periodic intervals, and the analysis server conducts a behavioral analysis of the data received from the sensor. The at least one relational database stores raw packet data, behavioral data, and index data.

Certain exemplary embodiments of systems of the present disclosure may include a plurality of sensors connected to the network. Also, two or more virtual private network tunnels connecting the sensor to the network may be provided in certain exemplary embodiments.

DETAILED DESCRIPTION

Figure 1:
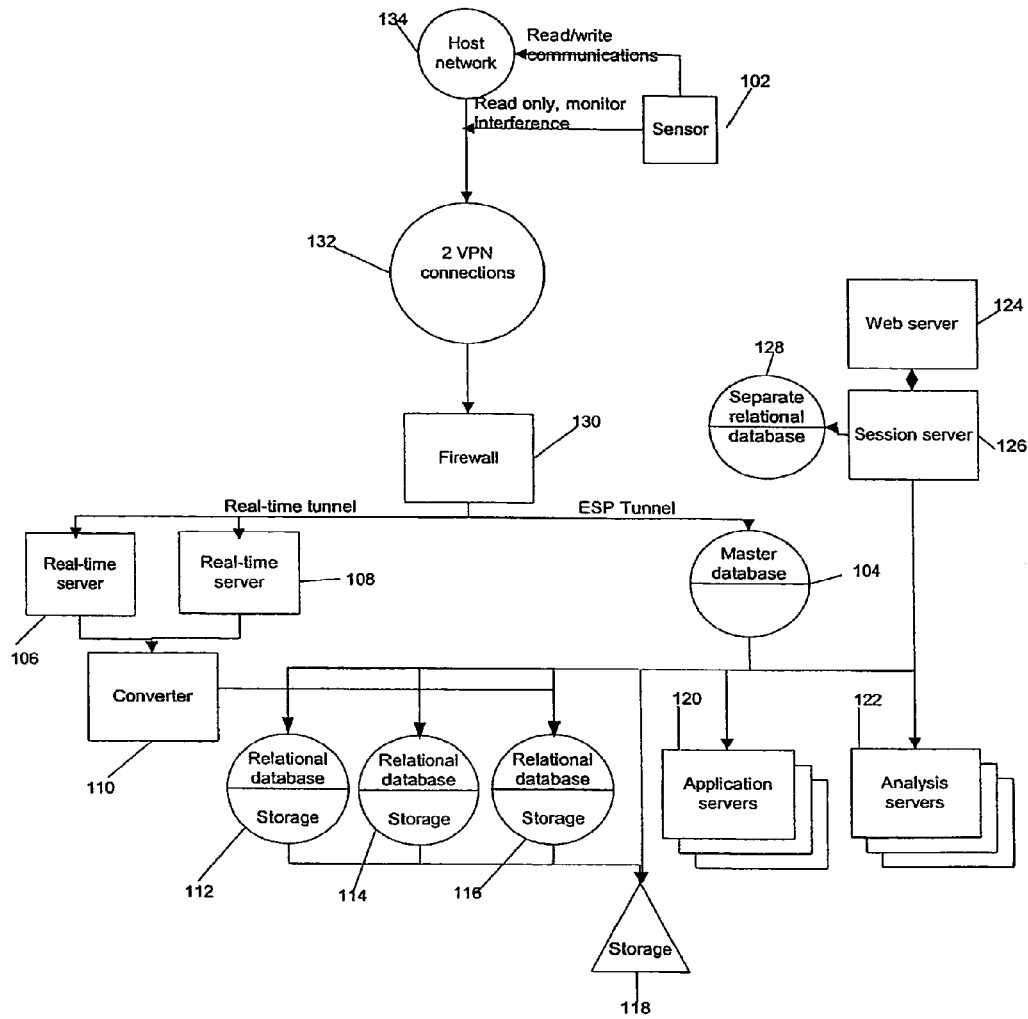
FIG. 1 is an exemplary environment for operation of systems and methods according to the present disclosure.

In describing embodiments according to systems and methods of the present disclosure, the following terms are used herein in the manner indicated below:

Agent: An IDS component that gathers system data, monitors system activity, and issues alerts upon detection of an intrusion.

Alert: A message sent by an IDS warning of a suspected or actual intrusion and usually calling for some sort of action in response. Also referred to as a notification.

Alert Generation: Addition of an alert to a database to record a detected event. All generated alerts are not necessarily displayed or released to an operator of the IDS, but generated alerts remain in the database.

Alert Release: Displaying an alert on a console for viewing by an operator of the IDS.

Console: An administrative or management component of an IDS. Often a graphical user interface (GUI) through which an operator or user controls operations of the IDS and where notification of alerts occurs.

Envelope: A two point data set that contains source and destination addresses in a raw packet.

Escalation: An alert is made a high priority.

Generation I statistic: A simple count of packet statistics. Also referred to as first generation statistic.

Generation II statistic: A count of a relationship between multiple generation I statistics.

Generation III statistic: A measure of a timed data point of a known resource (i.e., how much or how often a statistic occurs in a given time frame). Also referred to as frequency.

Intrusion: A violation of a system security policy by an unauthorized outsider or by an otherwise authorized user. A violation may include improperly accessing the network, accessing certain systems within the network, accessing certain files, or running certain programs.

Intrusion detection system (IDS): An automated system that can detect a security violation on an information system or network.

Normal: This indicates acceptance to a network and is network and sensor specific, meaning that what may be abnormal on one network may be readily accepted on another.

Prediction: A calculated value that is a guess of a future data point. This is not to be confused with curve fitting.

Protected Network: A range of addresses a sensor considers internal. Anything with a source outside this range is considered external. Anything inside this range is considered internal.

Protocol: A set of formal rules describing how to transmit data, especially across a network. This is a low level protocol defining bit- and byte-ordering and the transmission, error detection, and correction of the bit stream. Examples are IP (internet protocol), IPSec, (secure internet protocol), TCP (transmission control protocol), UDP (user datagram protocol), ICMP (internet control message protocol), ARP (address resolution protocol), and others which are well known to those skilled in the art.

Raw data: Actual packet headers up through layer 4 (64-bytes) stored in a file. Raw data is captured on a sensor and transferred to servers for import into a database. Once transferred to the servers, the raw data is no longer necessary.

Raw packet: Data pulled from a network packet and stored in a database in a field by field schema.

Resistance to Change (RTC): The resistance of any tracked data point to being changed by an analysis routine (i.e., the data point's predictability). A data point with a high predictability resists change because it has been judged correct many times before. A data point with a low RTC is typically unpredictable because it has a high rate of change.

Resource: A usable function of a network device, including servers, protocols, and services.

Rule: A set of selection criteria used to select raw packets.

Score (SCR): A human rating of any tracked data point Similar to strength but carries a heavier weighting when determining how normal a data point is. A small change in score is the equivalent of a large change in strength. This value can only be changed manually by an operator of the IDS.

Sensitivity: A global adjust that may be used to make a sensor more or less sensitive to certain types of alerts, such as resource, signature, threshold, and the like. Sensitivity can be used to tune a sensor to better fit a particular network.

Sensor: A device placed on a host network to monitor. A sensor may perform two functions: knowledge-based intrusion detection and packet logging of behavioral packages. A sensor collects raw packet data and behavioral data necessary to perform any analysis. This includes alerts, raw packets, thresholds, frequencies, attackers, and the like. The data collected remains separate for each sensor, but has the same format and schema.

Server: A network device having an address and transferring data on a network.

Service: A high-level protocol that specifies a function that is carried by a low level protocol. An example is HTTP (hyper text transfer protocol) carried by TCP, DNS (domain name server) carried by UDP, or an Echo Reply ICMP packet.

Strength (STR): An IDS rating of any tracked data point that judges the data point's normalcy to the network. Typically, low values indicate normal and high values indicate abnormal.

Strength-Score Value (SSV): A calculated value that indicates the severity of an alert regarding its danger to the host network. Every alert has an SSV that indicates the threat assessment of the source of the alert This value is calculated using the strength and score of the alert and the alert's source. Typically, the higher the SSV, the higher the threat.

Threshold: A bracket of a data curve that brackets both above and below the data points, indicating the curve's normal values. A threshold contains four data points for every data point on the tracked curve. Two points are a close estimate of the curve (a thin bracket that is usually within 3-5% of the normal data point) and a second more conservative estimate that is a wider bracket (usually with 6-10% of the normal data point).

Systems and methods according to the present disclosure provide the ability to analyze historical network traffic and determine which traffic does not belong in a network. Intrusion detection is performed over a period of time, instead of examining information quickly and never again seeing the information. Systems and methods of the present disclosure look for behavioral patterns within networks or information systems and generate alerts when these patterns change. Normal traffic behavior is collected on a continuing basis to establish a baseline for comparison with future network traffic. Once a statistically significant sample of historical data has been compiled, a behavioral intrusion detection agent is activated. The intrusion detection system intelligently forms correlations between disparate sources to find traffic anomalies. Over time, behaviors are predictive, and the intrusion detection system attempts to predict outcomes, becoming proactive instead of just reactive.

Intrusions occur throughout whole information systems, including both network infrastructure and application servers. By treating the information system as a whole and performing intrusion detection across it, the chances of detection are increased significantly.

The analysis of network-wide events is difficult because the data comes from very dissimilar sources and analyzing the source data is challenging. Any deviation in the normal behavior of the information system is a sign of possible intrusion. The data comes from sources including servers, network sensors, and firewalls, not just a single source. Once captured, source data (e.g., raw packet data) is stored and analyzed over a first specified period of time, and behavioral events (e.g., alerts) are stored and used for analysis for a second, longer specified period of time. One example is a one month first period of time and a one year second period of time. It should be understood that each of the time periods may be varied according to the preferences of the IDS users and operators.

Sources of attacks are stored long-term in a historical database along with an indicator of their hostility to the host network. This allows all further anomalies and alerts to be escalated to indicate that the attack was not a single, isolated event but a repeat from a known attacker. Additional attacks, in turn, raise the indicator leading to faster escalation, while periods of inactivity from the attacker lower the indicator. Attackers are removed from the historic database only when they have decayed to point where they have reached a negative indicator below a predetermined value. This value is a software setting. Higher values track attackers longer and lower values release them from the database sooner.

Additional features of an IDS according to this disclosure may include: analysis of bit-level packet detail; correlation of packet anomalies against IP-independent attack profiles; easy adaptability that includes signature intrusion detection systems; time based analysis that correlates profiles against packet anomalies; port access attempts correlated by both time and sequence; and traffic data stored in and processed from a relational database (RDB).

An exemplary environment for operation of systems and methods according to the present disclosure is shown in FIG. 1 and includes a master server (also referred to as master ESP server), at least one real-time server, at least one converter, at least one relational database (RDB), at least one application and analysis server, a web server, a session server, and a sensor (also referred to as an ESP sensor). Exemplary functionalities of each of these components are discussed below.

A master server serves an ESP database 104. Among other things, the master server keeps track of the job list, including pending, completed, and in-process jobs, and handles cooperative process-locking. The master server may also distribute sensors over RDB servers, stores global configuration values, stores sensor master variables (static configuration values for each sensor), and stores user accounts. In the embodiment shown in FIG. 1, a session server 126 acts as the master server. It is well understood by those skilled in the art that any appropriate server may be the master server. Servers such Oracle or MySQL servers or other standard hardware running Linux/Unix based operating systems may be used for the master server, as well understood by those skilled in the art.

As shown in FIG. 1, real-time servers 106 and 108 accept sensor connections for real-time alerts. Real-time servers 106 and 108 maintain the sensor real-time tunnel (network connectivity), store real-time data in native format (native to signature system: Dragon, Snort, etc.), store logged data from events (actual data capture at time of event), rebuild data sessions for application servers, and may also act as converters. Real time servers are standard servers, well known to those skilled in the art, running Linux/Unix based operating systems. Typically, they may include a dual-processor based system with a RAID array disk unit and a network file system, such as CODA, CIFS, or NFS, if the disk storage is not already network-based, all of which is well understood by those skilled in the art.

A converter 110 reads real-time alerts from native formatted files, connects to a sensor's RDB (such as RDBs 112, 114, and 116), converts alerts from native signature format to unified format, and may combine multiple sensors into a single ESP sensor. Converter 110 is standard hardware, well known to those skilled in the art, running Linux/Unix based operating systems that is able to mount network shared file systems and appropriate client software to connect to the RDBs. Relational databases 112, 114, and 116 (RDBS) store raw packet data, store behavioral data, and index data. RDBs 112, 114, and 116 send server data to web servers (such as web server 124), application servers (such as application server 120), and analysis servers (such as analysis server 122). RDBs 112, 114, and 116 accept data from converter 110. Additional storage, such as storage 118, may also be provided for storage from RDBs 112, 114, and 116 or database 104. RDBs 112, 114, and 116 may run on standard SQL-based database servers, such as those from Oracle or MySQL, which is well understood by those skilled in the art. The RDBs may typically have 1 GB of RAM per processor, and some configurations may include a storage area network (SAN) or network attached storage (NAS) for central database storage.

An application server or servers 120 stores the system's backend user interface code, serves application data to web servers (such as web server 124) and other user interface systems. Application server 120 may serve any sensor. An analysis server or servers 122 looks for pending jobs, locks jobs, marks jobs in-process, performs analysis jobs, stores results (update behavioral profile), marks jobs processed, and unlocks jobs. Application server 120 and analysis server 122 may be combined in a single server. Application and analysis servers include standard hardware running a Linux/Unix based operating system with appropriate client software to connect to the RDB servers, as well understood by those skilled in the art. Open SSH, which is well understood by those skilled in the art, may be used if encrypted communications are required from the application and analysis servers to any web servers.

A web server 124 processes web requests, calls application server applets to produce application data, and handles user interfaces. Web server 124 may not access sensor data. A web server is standard hardware, well known to those skilled in the art and typically runs on a Linux/Unix based operating system with appropriate client software to connect to RDB servers. Session server 126 handles web server session keys, stores session data, deletes old sessions (stale), and handles accounts. As noted above, session server 126 may, in some instances, be the master server. Standard server hardware may be used for the session server, such some of the servers described above, as is well understood by those skilled in the art A separate relational database 128 connected to web server 126 may be provided.

A sensor (or ESP sensor) 102 includes three separate subsystems designed to perform three functions: signature checking, data capture, and security. Each sensor is a bastion host containing an internal firewall, a knowledge-based sensor, and a packet logger. The knowledge-based sensor is designed to handle signature detection only, and leaves the anomaly detection to the IDS analysis servers. The packet logger has complex filtering capabilities that can be used to capture only the desired data, but this is rarely employed. The more data the system captures, the better the analysis. Typically, sensor 102 includes a single or dual processors (for larger networks) and two network interface cards. Standard hardware runs Linux 2.4+ with the Linux socket filter, sock packet and ipchains features enabled. A virtual private network tunnel or other transport tunnel is necessary to move data from the sensor to a server. As noted above, OpenSSH may be used to transfer behavioral packages to conversion and import servers.

Sensors are designed as bastion hosts because they are employed in perimeters in front of any security devices. Typically, the sensors operate with a read-only wire for the sensing interface, but a second network interface handles communications with the console, and as a security device, this interface must be well protected. The internal firewall is used to protect the communications interface and to protect the sensor for denial of service attacks using traffic shaping techniques. All packets on the communications interface are fully defragmented before being passed to the remainder of the IDS.

As noted, sensor 102 includes a packet logger. On very high-speed networks, any analysis on the sensor hinders performance of the sensor and can lead to dropped packets. For these reasons, the behavioral analysis occurs offline. The packet logger creates "packages" of compressed and encrypted traffic that is sent back to the analysis station at specified intervals, for example 30-minute or 60-minute intervals. Each package is unencrypted, decompressed, and fed into the behavioral analysis portion of the IDS, as further described below.

The packet logger reads packets from the network interface, classifies the packets by protocol, compresses the packets, and writes them to a disk using a double-buffered, threaded process. The analysis relies mainly on traffic patterns of a network, so the data is not necessary. Though there are reasons to log the data, it is not essential for behavioral analysis. On very high-speed networks, the sensor can be split into two parts, with one performing signature checking with a knowledge-based sensor, and the other performing packet logging. This allows for maximum speed for each data source and packet logging to speeds of 180+ Mbits.

A firewall 130 hides the remainder of the IDS from host network 134 and protects sensor 102. Any standard state-aware firewall well known to those skilled in the art is acceptable for use. Firewall 130 also splits traffic to the various servers, as shown in FIG. 1. Sensor 102 initiates virtual private network (VPN) tunnels 132 to firewall 130. VPN tunnels 132 include a long term encrypted tunnel for real time alerts and a short term tunnel for transactions that connects when data needs to be transferred and disconnects when data transfer is complete. In one embodiment, data is transferred using two tunnels and maintenance is performed in a non-real-time mode. In other words, the IDDS transfers knowledge-based sensor alerts through a knowledge-based sensor tunnel and all sensors share a single tunnel for raw alert storage on the real-time server. In another embodiment, an e-tunnel allows for the use of any signature-based product with a behavioral system. Additionally, the e-tunnel allows for transfer of multiple growing files to the server, handles multiple input and output streams, creates and maintains a VPN tunnel (robust encrypted network connection), performs system maintenance remotely and securely, reports on system status (performance monitoring), and provides each sensor with its own data store on the server.

Sensors typically communicate back to the remainder of the IIDS using a secured method. Network sensors minimally employ a 640-bit encrypted TCP tunnel. The communications key is changed periodically, e.g., hourly. Authentication occurs using, for example, a 768-bit certificate on both sides of the tunnel. The firewall only allows connections between the registered analysis station and the sensor, the tunnel application verifies the host Internet address, and both Internet addresses are used in key generation and authentication exchange. Remote sensor administration is performed through the same 640-bit channel. All communications to the sensor, including performance monitoring, are fully encrypted and authenticated through the same mechanism.

Figure 2:
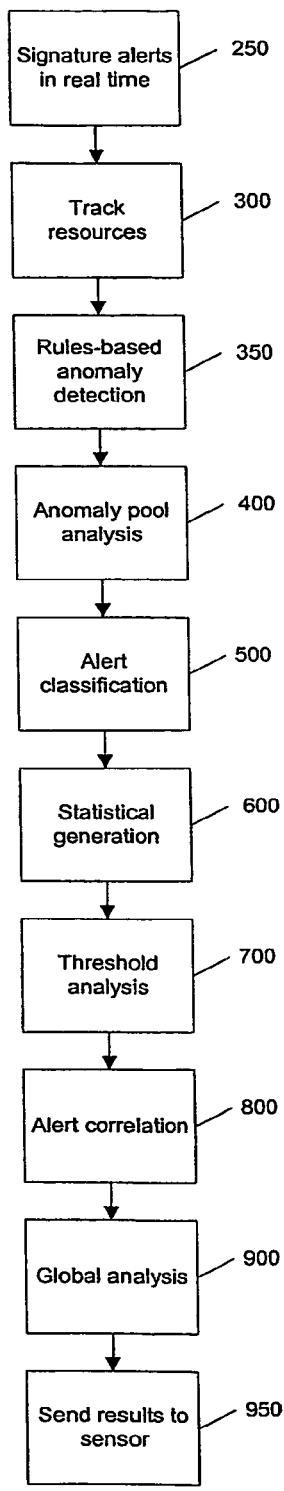
FIG. 2 shows an overview of process flow of an embodiment according to systems and methods of the present disclosure.

FIG. 2 provides an overview of process flow of an embodiment according to systems and methods of the present disclosure. In an exemplary process 200, knowledge based intrusion detection including sending signature alerts in real-time, block 250, is included. The function of knowledge-based intrusion detection is to perform real-time vulnerability checking of packets that are passed through the firewall. The knowledge-based portion of the sensor is charged with data inspection and alert generation from signature checking. Similar to virus checking, a sensor looks in network packets for known strings and series of bytes that indicate attacks. Alerts appear on the console in real-time. The alerts are automatically prioritized by information contained about the source address in the behavioral database, whereas most signature-based processes prioritize alerts by type (alert name) only. The signature-based alerts are escalated from their default priority as necessary based on the source's strength, score, and the signature sensitivity setting for the sensor.

Behavioral analysis includes block 300 through block 800. In blocks 300 through 800, behavioral analysis is performed for an individual host information system (a collection of related sensors). Finally, global analysis occurs at block 900 and includes behavioral intrusion detection over sensors across multiple information systems in order to help find hackers across the Internet. This can identify scanning sources and coordinated attacks.

Behavioral analysis includes adaptive rules-based profiling using model-based reasoning. Behavioral patterns are abstracted by describing them as sequences and thresholds stored as historic rules. Current behavioral patterns are then checked against the historically predicted patterns and deviations are noted. Some deviations can be classified at the abstract level, while others require the IDS to find the associated source data and perform rules-based source analysis. Behavioral analysis uses information in the RDBs with the goal of detecting all intrusions. The sensor is connected to the remainder of the IDS and transfers the logged packets to the analysis server. Each packet is decompressed and imported into the RDB for the particular sensor, and analysis then begins. Since analysis is rule-based, once the data is ready, processing can be split across multiple servers allowing analysis to occur on clusters.

As shown in FIG. 2, behavioral analysis includes numerous steps. Resource tracking, block 300, is a process that discovers network information by examining the host network traffic. The analysis server looks for servers, protocols, and services and records them in the database. After being recorded, these services, protocols, etc. are tracked in the future and statistics about them are gathered. This process is continuous, so new resources are discovered and old resources are deleted, generating alerts in either case. By listing this data, systems, protocols, and services in use at any given time are identified and a measure of how important they are to the host network is provided.

Rules-based anomaly detection, block 350, includes using a series of rules to find anomalies on the network. At this point, anomalies are individual packets that match selection rules that define such things as illegal packets, unusual packets, and normal packets that are not sent to valid network resources (e.g., http requests to a server that does not service http). These packets are collected and added to the database in a protocol independent area called the anomaly pool. There are a series of normal rules that then subtract known normal packets—this accounts for anomalies that are accepted as normal in the particular host network.

Also included in stage 2 is anomaly pool analysis, block 400. Once an anomaly pool is created, the packets in the pool are examined independently of the selection process. This may be referred to as "blind" analysis because this analysis is carried out without the server having any knowledge of why the packet was added to the anomaly pool. For instance, if a rule added packets because the packets have an unusually low time-to-live (TTL), it would be simple to generate an alert that says "LOW-TTL." However, this is biased, and presupposes a LOW-TTL and nothing else about the packet. By examining the packet blindly without knowing why the packet was added to the anomaly pool, the blind analysis attempts to determine why the packet was added. This leads to relationships between packets and anomalies that indicate base-cause issues and is comparable to a pathologist finding the origin of a disease as opposed to just treating the symptoms. The blind analysis aids in finding new attacks because when the entire anomaly pool cannot be accounted for, human operators of the IDS are notified to conduct further analysis to determine why this is the case. The result is generation I anomaly alerts that are classified, block 500.

At block 600, statistics are generated. Generation I statistics are generated, which involves a simple counting of various aspects of protocols, such as number of packets, incoming packets, outgoing packets, categorizing packets into various sizes, etc. These statistics are referred to as generation I because they varying and are less predictable. Generation I statistics do not show relationships of traffic flow, but they provide a volume baseline. Next, generation II statistics are created. This process, using protocol and service models, relates statistics to create more predictable values that show traffic flow as opposed to volumes. For instance, a comparison of inbound ping requests to outbound ping replies may be made. Generation II statistics illustrate a relationship between packets that creates a predictable traffic flow. The difference between these values as a percentage of the packets is almost always a predictable value on networks. Generation II statistics are stored in the database. Generation III statistics (also called frequencies) are calculated as well, counting resource usage values and envelope pairings that track which resources are used by which systems.

Threshold analysis is performed at block 700. Threshold values are stored based on historical data. Threshold violations tend to show large problems, but determining metric overflow and underflow values is difficult. For this reason, sequences of values are often aggregated together using the model-based reasoning system so that threshold indicators are dependent on more than one possible value. If the abstracted threshold fails, the source data is examined and compared against the model rules once again. Since data is compared in the abstract layer to historical data, historical source data is necessary for full analysis. For each statistic, both generation I and generation II, each value is checked against the most recent prediction. If it fails, an alert is generated. New predictions for the next time interval (e.g., an hour) are calculated and stored. Generation II alerts are weighted heavier then generation II when creating alert prioritizations. Frequencies are checked by threshold predictions. Any remaining violations are added to the alert pool and submitted for adaptive classification.

After threshold analysis is complete, alert correlation occurs, block 800. Alerts are correlated by type using statistical analysis of the types of alerts received. The correlation measures the number of alerts of various types and relates increases and decreases of alerts and their relationships to the percentage of the whole. The correlation is then performed for all alerts on the specific network. Related sensors are analyzed and alert relationships by source of alert (attacker) are noted. Attackers are recorded and tracked in each individual sensor. Upon completion of alert correlation, behavioral analysis for a particular sensor is complete.

Global analysis, block 900, includes analysis of all available sensors as if they were on one large network. For example, if an IDS provider services one hundred networks or information systems, the global analysis may be performed for all sensors on these one hundred networks. Global analysis begins with the grouping of all alerts from all sensors into a common alert pool. Where alerts are generated becomes irrelevant, only the alert types and sources are significant. The common alert pool is then examined by alert type and by source, similar to the steps performed in the behavioral analysis for each sensor. This yields new prioritization values of both attackers and alert types. This new information may then be sent to the sensors to help prioritize alerts on a per sensor basis, block 950.

More detailed information about certain exemplary embodiments of processes in blocks 300-950 of FIG. 2 is shown in FIGS. 3-9 and described below.

Figure 3:
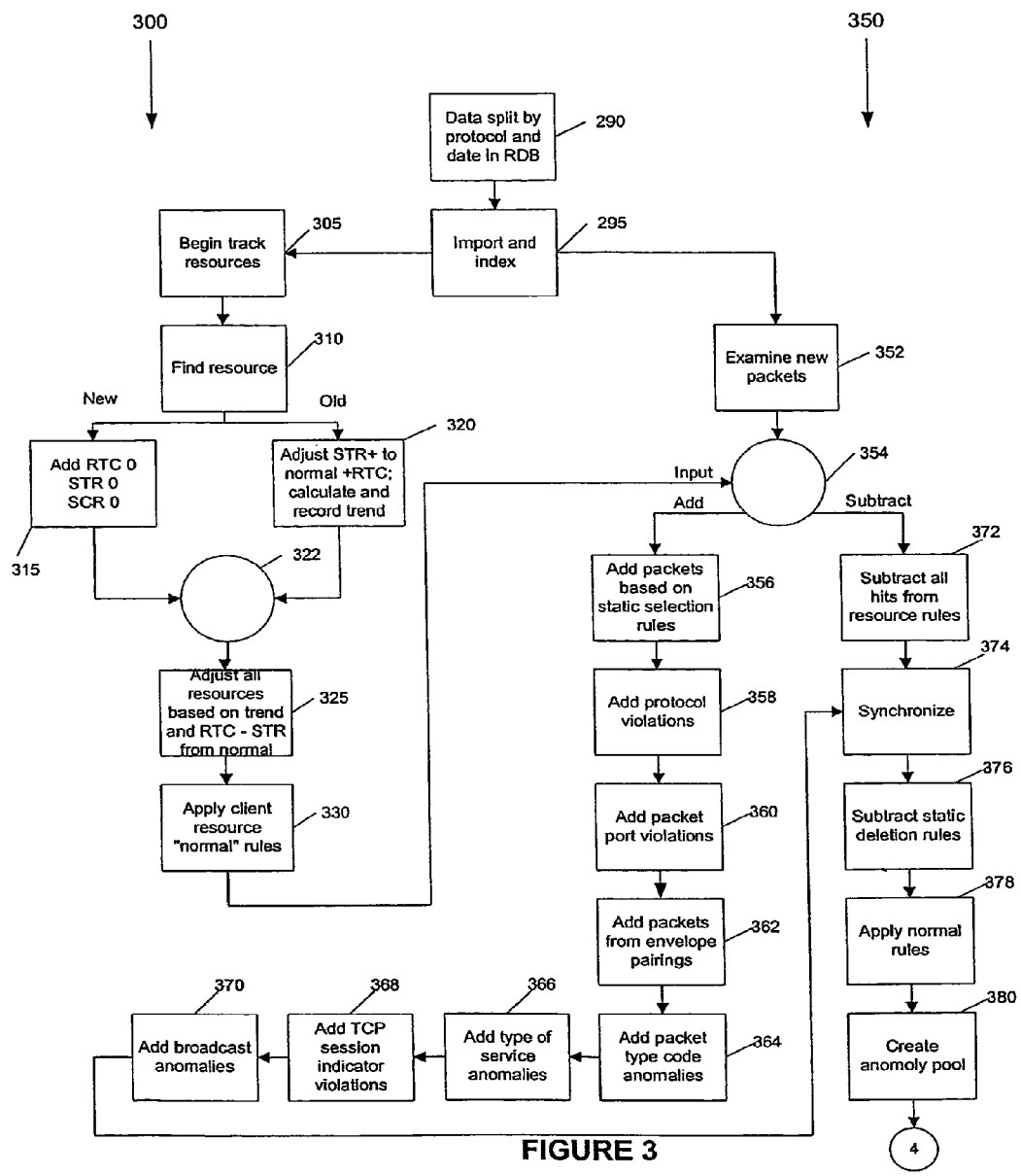
FIG. 3 shows process flow for an embodiment of resource tracking and rules-based anomaly detection according to systems and methods of the present disclosure.

Referring now to FIG. 3, process flow for an embodiment of resource tracking 300 and an embodiment of rules-based anomaly detection 350 according to systems and methods of the present disclosure are shown. Initially, data is split by protocol and date in an RDB server, block 290. Periodically (e.g., hourly, bi-hourly), packets collected on a sensor are sent to the RDB server. These packets are split by protocol (e.g., ICMP, IP, TCP, and UDP) and inserted into the database. A filter may be applied at the time of import to selectively insert only certain packets, which is helpful in specific situations where it is not desirable to send certain packets to the database. At block 295, import packets are indexed in the relational database.

Resource tracking begins at block 305. Resource tracking examines the raw data and finds resources on the host network. Resources are found, block 310, using protocol models. Multiple algorithms pass through the raw data finding resources. Some are simple, such as looking in the protected network for internet addresses that indicate servers. Others are more complex and require examining data flow to find the protocols and services. Resource activity is verified by finding two-way conversations, not simply looking for outbound traffic. The conversation is verified by finding evidence of traffic moving to and from systems that appear to be servers. For some protocols, this is a statistical analysis, and for others it is a search algorithm.

At block 315, if the resource is a new resource (i.e., the IDS has not previously "found" this resource), an alert is added. The resource is added to the resource database with its STR, SCR, and RTC set to zero. If the resource is already listed in the database, block 320, its STR increases. If the resource was found within a predetermined time (e.g., the last hour), the RTC is incremented. Once all new and old resources are analyzed in blocks 315 and 320, the resources are pooled together, 322, and resources that are in the database but were not modified lose STR, block 325. The decrease in STR is inversely related to the RTC. Resources with high RTC lose little STR, while resources of low RTC decrease rapidly. At block 330, client resource normalizing rules are applied. Because some systems or certain protocols or services are rarely used, a mechanism to allow overrides is included. To accomplish this, a set of static normalizing rules define resources that do not change and/or resources that are not to be added.

Rules-based anomaly detection 350 begins at block 352 with examination of new packets. All raw packets are examined for anomalies. Two types of anomalies are searched for: anomalous packets and normal packets that should not occur on the network. These packets are added to the database in a table, known as the anomaly pool, that is protocol independent. A resource list output from resource tracking 300 is added to the new packets, 354, and rules of rules-based anomaly detection are applied, at blocks 356-368, to find anomalous packets. The first rule applied, block 356, is adding all packets that match static selection rules. Static selection rules add to the anomaly pool anything that matches. These are normally added to track traffic that is completely normal, but is being tracked for some external reason, such as alerting all traffic from a particular source. At block 358, all protocol violations are added. Protocol violations are problems with packet data that are not allowed by the protocol specification or are not specified by the RTC. These packets are not normal to a network because they violate the protocol rules, but can still be routed on a network.

Packet port violations are added at block 360. Packet violations are usually protocol violations, but are found by the IDS in a different manner. Unlike protocol violations, packet port violations are packets dropped off the network by hosts upon delivery. The packets are so malformed they are dropped completely, such as a layer specifying that layer 4 is TCP when the packet does not conform to TCP. At block 362, packets from envelope pairings are added. These are packets that could not have been generated or delivered to the host network and are very often the result of spoofing activity or an envelope specifying the same source and destination. Type code anomalies are also added, block 364. All ICMP packets have a type and a code that specifies what type of message the packet is carrying. Type code rules find illegal or strange type code combinations.

At block 366, type of service (TOS) anomalies are added to the pool. The TOS field is a part of the IP protocol. Only certain values can be in the TOS field and any value outside of these specified values is suspect. At block 368, TCP session indicator violations are added. TCP state indicators are bits within protocols that are used to indicate or store the information necessary to the protocol during normal use. Many protocol specifications only specify what the indicators are used for, but not how to deal with conflicting indicators or unused bits in the indicator space.

Because broadcast traffic has no specific destination, broadcast traffic is examined separately and packets are added, as necessary, based on protocol models, at block 370. For instance, TCP to broadcast addresses is not supported and should not be found on a network.

While blocks 356-370 relate to adding anomalous packets to the anomaly pool, block 372 subtracts normal packets from the pool. To find normal packets that meet all specifications and are free of violations but that are sent to or originating from the wrong resources, all raw packets are considered and those that originate properly and have come from proper destinations, as compared to the resource list from resource tracking, are removed. This removes all expected traffic from the raw packets. The remaining packets are added to the anomaly pool for analysis. At block 374, synchronization is performed to ensure that all add (blocks 356-370) and subtract (block 372) rules are complete before continuing.

Once again, some traffic added to the anomaly pool may be considered normal to a particular network, so a set of static deletion rules removes all matching traffic from the anomaly pool, block 376. At block 378, normal rules are applied. Normal rules are code-based, specific algorithms that handle special known situations, such as protocol stacks that generate certain anomalies and the like. The anomaly pool is complete, block 380, and all packets are marked "unclassified."

Figure 4:
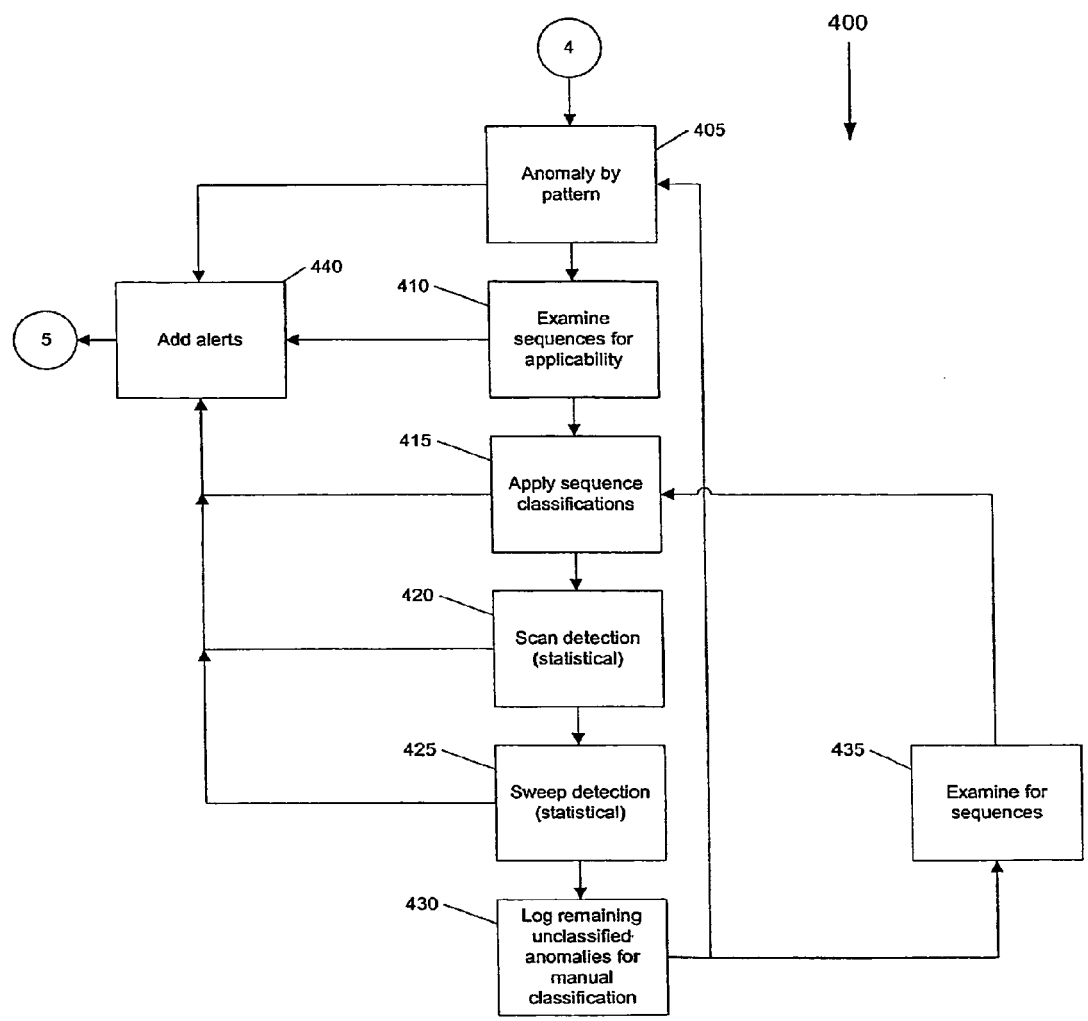
FIG. 4 shows process flow for an embodiment of anomaly pool analysis according to systems and methods of the present disclosure.

FIG. 4 shows process flow for an embodiment of anomaly pool analysis according to systems and methods of the present disclosure. As anomaly pool or "blind" analysis 400 begins, the anomaly pool is full of suspicious traffic to be analyzed and classified. Without knowledge of why the raw packets are in the pool, routines now try to classify each anomaly or set of anomalies. The first set of routines are anomalies by pattern, block 405. This is a series of code-based algorithms that classify packets based on known patterns. These algorithms may be developed using previous unsuccessful attempts to classify packets using the steps at blocks 405-430. Any packet or set of packets that matches these patterns is marked as "classified" and appropriate alerts generated, block 440. A standard add alerts routine is called to create alerts with adjusted SSV for display on the console. These alerts are available for viewing.

At block 410, analysis continues with the examination of sequences. Sequences are events in order of time. The examination of sequences looks at anomaly pool-based known sequences and is a traffic flow analysis based on known protocol and service attack models. This is a data driven list of events to look for in the proper sequence forward in time. If any known sequences are found, those classifications are applied, block 415, the alerts are marked classified, and alerts are added to the console, block 440. At block 420, a scan detection routine is run. This statistical routine analyzes the distribution of destination ports over source addresses. A source hitting a high number of ports is port scanning, and the number of destinations determines whether a single host or multiple hosts are scanned. If scans are found, alerts are added to the console, block 440.

Sweep detection, block 425, uses a statistical routine to find sources attempting to access a single service on multiple servers, which indicates a sweep. If sweeps are found, alerts are added to the console, block 440, and the packets are marked classified. Any remaining alerts in the pool are unclassified and are classified by human analysts, block 430. These packets are logged and submitted for review. New classifications may be entered as sequences or anomaly patterns. All unclassified anomalies are scanned for sequences that are entered into the sequence list, block 435. This list can be reapplied to further classify remaining anomalies.

Figure 5:
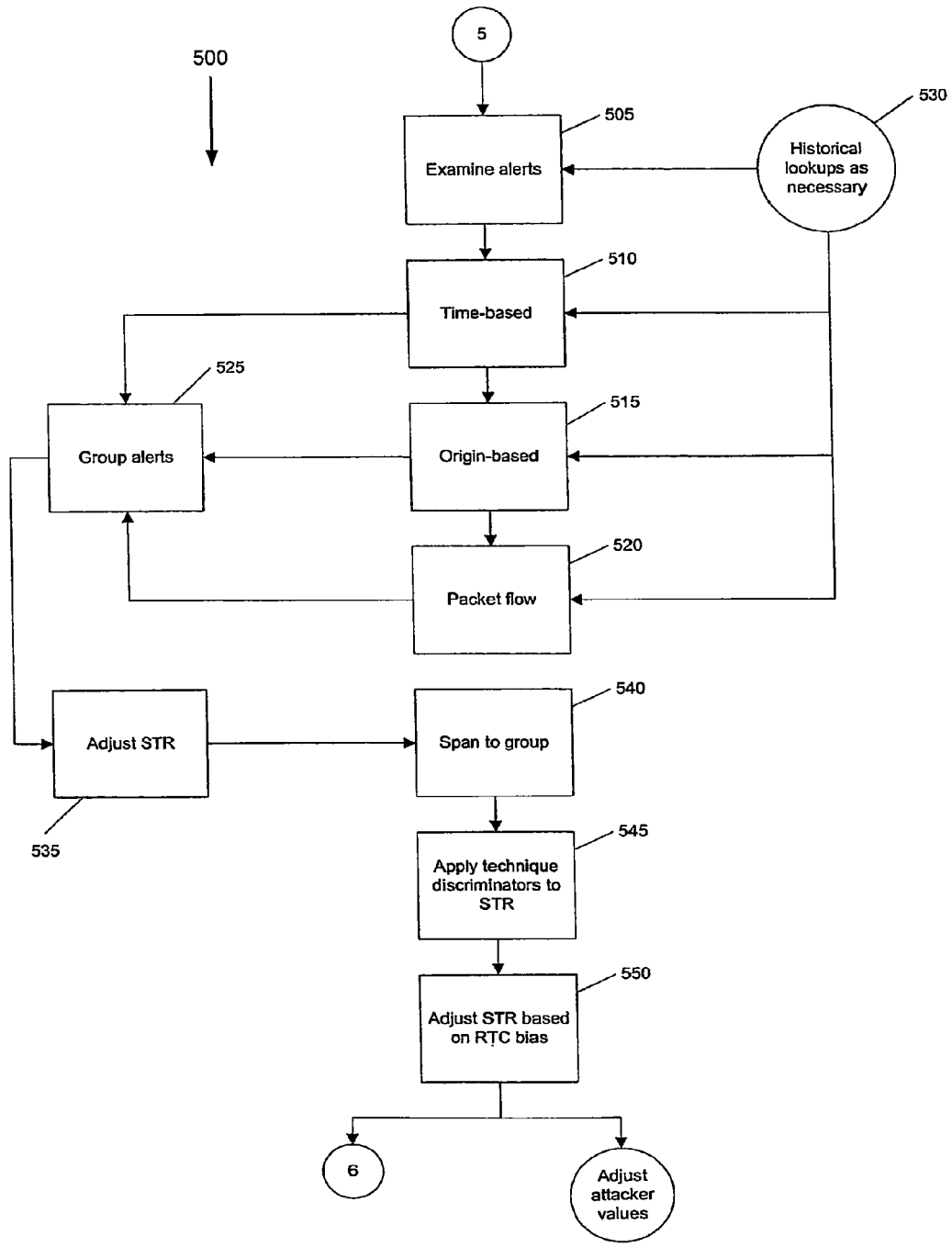
FIG. 5 shows process flow for an embodiment of alert classification according to systems and methods of the present disclosure.

FIG. 5 shows process flow for an embodiment of alert classification according to systems and methods of the present disclosure. Alert classification 500 begins with examination of signature alerts at block 505. All alerts generated for a specified time period (e.g., an hour, two hours, etc.) are analyzed for further correlations in an attempt to generate more useful alerts. Alerts are grouped by time and the number of alerts are counted for high activity periods, block 510. Extremely high numbers indicate further analysis is necessary. Active periods also indicate times a hacker may choose to work, which is often a detectable pattern that can be used to find hackers when they switch addresses or attack origins.

Alerts are grouped by source, block 515, over time using historical data. This allows the IDS to find slow activity where the attacker is performing actions slowly in an attempt to stay hidden by not generating alerts quickly. Such things as slow port scans, slow vulnerability probes, and slow attacks may be found. The attackers' database from the add alerts routine already tracks individual sources, so this analysis focuses on slow activity. At block 520, packet flow correlation is examined, also known as backscatter. Here, protocol models are used to examine packet flow. Communication sessions may be examined and compared to normal models to find deviations. Spoofed traffic on the host network, as well as the residual traffic generated when the host network's addresses are externally spoofed, may be found. As shown in FIG. 5, historical look-ups, 530, may performed for assistance as necessary among blocks 505-520 by the IDS.

All historical alerts are grouped by source and counted to determine the degree of activity for any source using any high frequency alerts, block 525. Once the processes in blocks 510-525 are complete, alerts are grouped by source and appropriate STR changes are calculated for each alert or time pattern, block 535. Alert patterns warrant high SSV increases, while time patterns results in only small adjustments. STR changes are applied to the attack sources, block 540. This increases the strength of all sources generating like alerts and results in higher SSVs for sources using like alert patterns or like times.

At block 545, technique discriminators are applied to STR—A static table contains a list of alerts and a number representing the skill level required to perform the type of attack that generates that alert. This is representative of the intelligence level of the hacker or, at the very least, the hacker's ability to know when to apply the appropriate hacking tool. Applying this number as a modifier to STR allows SSVs to be affected by attacker skill in an attempt to highlight stealthy or intelligent hackers that are above average. This is known as a "technique discriminator." The actual value of the technique discriminator is static and assigned by human analysts. The value may be used globally across multiple sensors and multiple protected networks.

A final step of alert classification is applying an RTC bias, block 550, which may be applied to any attack source. Most attack sources have no RTC assigned or tracked, but in some cases, it may be convenient to apply an RTC bias to certain attack sources to prevent a planned one-time event, such as a vulnerability scan, to affect attacker profiles. It is typically easier to adjust the score to a low number before the event and reset the strength and score when the event has occurred. Because this is effective, RTC values are not stored for every attacker.

After alert classification 500, two remaining processes may be performed in parallel. Statistical generation and threshold analysis, which are shown and described in FIGS. 6 and 7, and adjusting of attacker values. An exemplary process of adjusting attacker values is briefly described below.

All origin-based alerts (i.e., alerts with a known origin) are generated and have calculated SSVs in the alert database (and have been shown on the console). Attackers that have ceased attacking slowly return to non-threatening status based on the maximum SSV calculated. Since this number is a combination of strength and score, reducing strength to zero will also zero the threat profile. Attackers slowly decay until they are removed and this is accomplished by reducing STR for any specified time interval (e.g., an hour or three hours) in which the attack source is not the origin of an alert. The last time an attacker was adjusted is stored, and, for any specified time interval in which an attacker is not the source of an alert, the STR is reduced by an amount that is calculated from the period the attacker has not generated an alert and the attacker's RTC (if assigned). In this manner, attackers that quit generating alerts slowly reduce in threat and eventually return to zero. It should be noted that this process is slow and SSVs continue to be high for some time (how long is based on the SCR) after the attacker has ceased the current attack.

Figure 6:
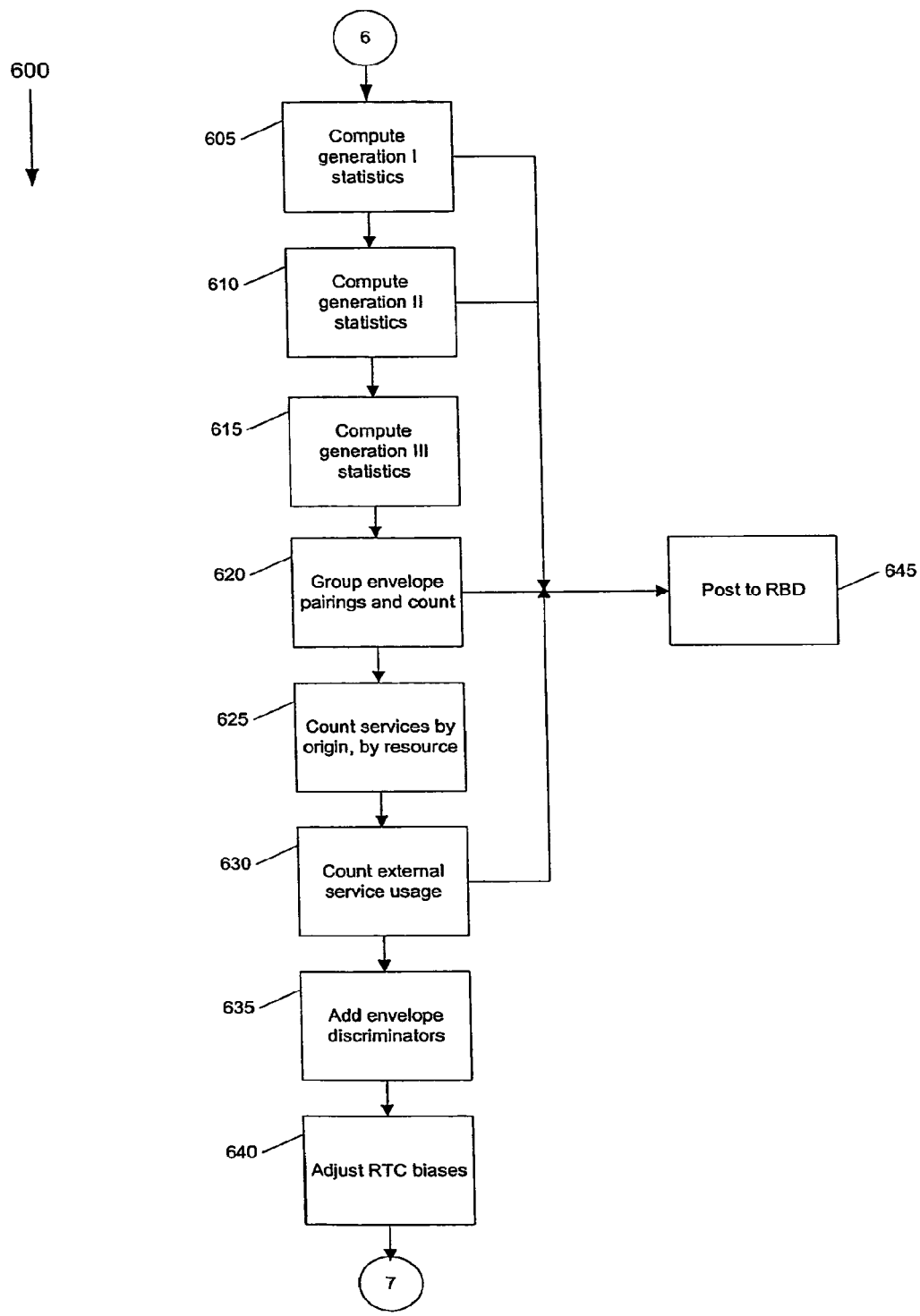
FIG. 6 shows process flow for an embodiment of statistical generation according to systems and methods of the present disclosure.

Referring now to FIG. 6, process flow for an exemplary embodiment of statistical generation 600 is shown. Generation I statistics are computed by simple counting of raw packets, block 605. Block 645 is a generic descriptor indicating that data is posted to the relational database. Generation I statistics are less predictable and therefore harder to track. Generation I statistics include counting frequencies of types of packets, such as the number of packets in each protocol, the number of incoming packets, the number of outgoing packets, the number of fragmented packets, and so on. Queries are made on the raw packets to determine these counts for a specified time interval (e.g., a half-hour, an hour). Some data flow analysis is necessary to determine some generation I statistics because certain protocols, such as TCP, require multiple packets to determine if sessions are valid or just attempted. Many generation I statistics are gathered and stored, resulting in continuous data curves that have periodic (e.g., hourly, daily) data points. The statistics to be gathered are based on the protocols analyzed. For generation I statistics, because the data points do not have to be predictable, gathering as many statistics as possible is the primary goal. If predictable values are gathered, it is advantageous, but values that are predictable for one network may not be predictable for another. Generation I statistics are stored in a separate table.

At block 610, generation II statistics are created from generation I statistics by finding relationships between data points. This is typically an operator (human) process, but is based on protocol and service data flow models. A standard set of generation II statistics may be generated by using the protocol models to find ratios and relationships. For example, comparing TCP packets with the SYN (synchronize/start) flag turned on in one direction versus TCP packets with the SYN-ACK (synchronize/acknowledge) flags turned on in the other direction. Generation II statistics use two or more generation I statistics to create more predictable values of related information by calculating and comparing ratios and differences over time on the network. Generation II statistics are stored in the thresholds table and calculated during threshold analysis (see FIG. 7 and accompanying description below). The step shown at block 610 is the recording and storing of values to use as generation II statistics using analysis tools that assist in finding useful, predictable generation II statistics.

At block 615, generation III statistics are recorded and stored. Generation III statistics calculate events over time. These are called frequencies because they track the occurrence of events over time. Three main types of generation in statistics are calculated: envelope pairings, service usage by resource, and external service usage. Over time, generation II statistics produce highly predictable curves if they are adapted as the network changes.

Envelope pairings are calculated by counting the number of times two systems exchange information. All envelopes are counted and grouped, block 620, by unique pairs of servers. For example, src to dst and dst to src are grouped the same. The number of unique conversations is recorded as a statistic. This shows which servers talk to which servers, and records the time of the events. At block 625, usage counts of service resources are made by examining the resource table and counting service usage per server. These values are recorded as a statistic and show the number of times each given resource is used on the protected network, including recording the time of the events. Service usage is calculated in an outbound direction, block 630, to profile what external services the protected network uses. This provides the external services used and number of times the services are used and records the time of the events.

All counts calculated in blocks 620-630 may be adjusted by a static discriminator, block 635, or removed entirely as a tuning mechanism for the sensor. Such adjustment or removal may be performed to remove such things as traffic generated from ad hoc backups that may distort the statistic in the historic database (because historic numbers are used to continuously adjust the predictions, such large changes may cause an imbalance for a lengthy period of time if not removed). At block 640, additional RTC changes are performed. Once again, this is a tuning mechanism used to force a static value onto an RTC to stop an ad hoc event from distorting values in the future. All statistical values are now calculated and may be compared as thresholds to the last time interval's predictions, as shown in FIG. 7.

Figure 7:
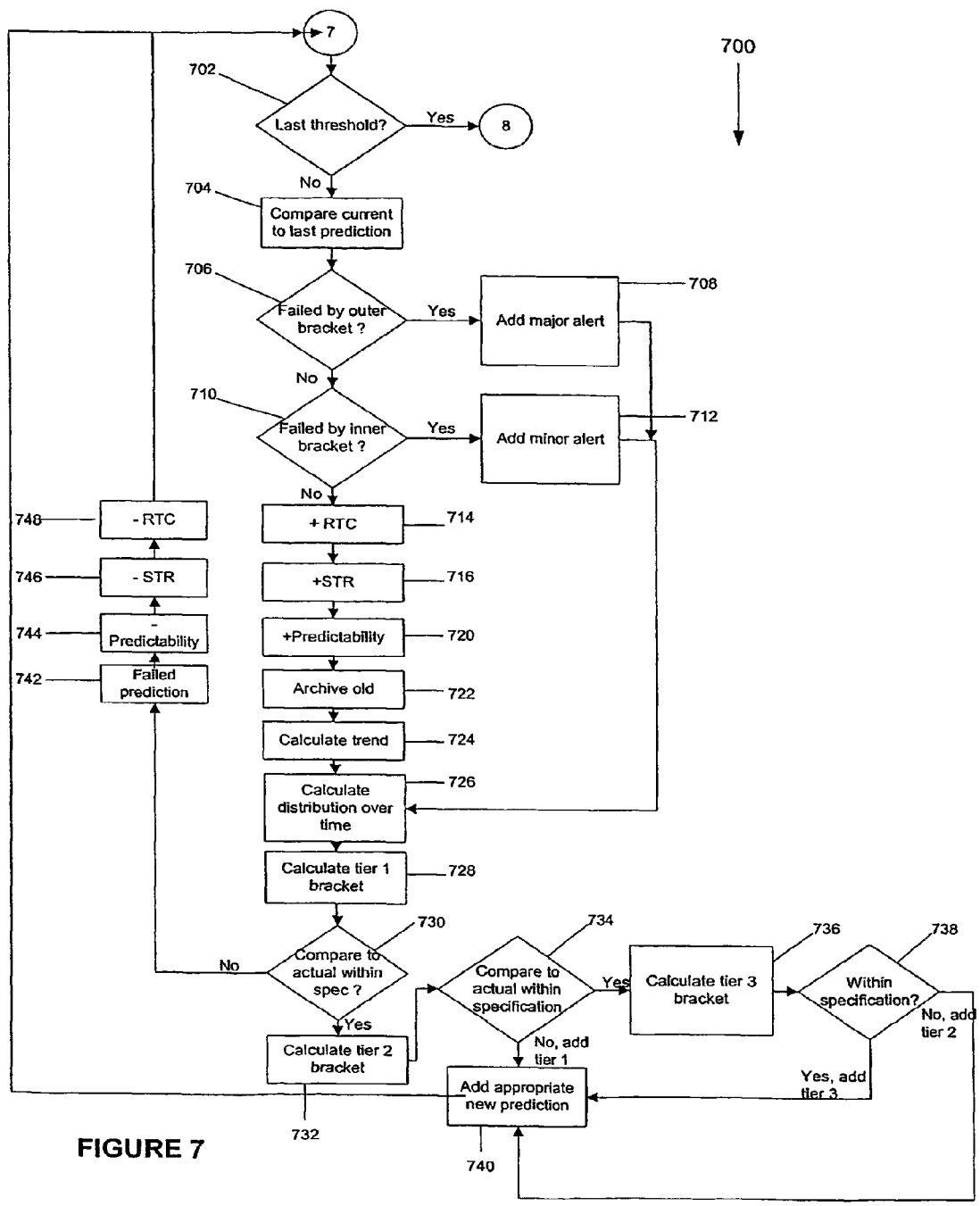
FIG. 7 shows process flow for an embodiment of threshold analysis according to systems and methods of the present disclosure.

FIG. 7 shows process flow for an embodiment of threshold analysis 700 according to systems and methods of the present disclosure. Threshold analysis includes a curve prediction algorithm that tracks data points over time in order to make predictions of future values. Threshold analysis may be used to track any statistical value, such as number of packets of a given protocol, or data points, such as the frequency of a particular alert from a given source. Statistical value refers to those values that come from counting events, for example, but not limited to, number of packets, number of UDP packets, number of failed TCP connections where an RST flag is detected, and others. The statistical values come directly from raw packet data. A data point originates from a pattern the IDS has detected, either automatically or by request from an operator of the IDS. Data points do not come directly from raw packet data, but rather are calculated from correlated events and represent any repeated series of events that occur in a predictable fashion (i.e., a pattern). Some examples include, but are not limited to, the number of times a particular server on the Internet generates a specific alert, the distinct number of times a worm visits the monitored network, and the average frequency of web-based attacks for a given server. Both statistical values and data points are treated in the same manner by threshold analysis.

Referring now to FIG. 7, this process iterates once for each threshold. A prediction is made for each collection interval. This prediction is then checked against the actual data, which may generate alerts. The threshold is then stored for future use along with the actual data to be used to calculate and adjust future thresholds. The last prediction made is stored in the threshold table (marked "prediction") along with all previous predictions (marked "archival"). In this manner, the predicted data curves are constantly changed as the network changes. All thresholds can be calculated, for example, continuously (all historical data points), by time ranges (e.g., from 18:00 to 07:00), or as individual hours (e.g., from 06:00 to 07:00) and each of these can be predicted. For each date-time range, there is a separate prediction. This allows for normal behaviors, such as outbound web usage increasing from 08:00 to 18:00 on weekdays (a very normal behavior if user workstations are in the protected network), to be taken into account.

Alert correlation begins against the predicted threshold (calculated at the last analysis run) in block 702. The current statistic or data point being analyzed is compared to the last prediction, block 704. The prediction consists of four values: the actual data point, the predicted data point, the minor offset, and the major offset. The data value is calculated using the new data received in the current data package (after all the statistics have been generated). The prediction of the current statistic/data point being analyzed is retrieved from the database along with the major and minor offsets. Adding the minor offset to the predicted value creates the upper limit and subtracting the minor offset from the predicted value creates the lower limit. This is done again with the major offset to create the major bracket. These values create two brackets above and below the prediction that provide a buffer for the prediction to succeed. The higher the predictability of the given statistic/data point, the narrower the minor and major offsets and the smaller the brackets.

A determination is made as to whether the current statistic or data point is outside the major bracket, block 706. If the current statistic is outside the major bracket, this indicates a major threshold overflow, if greater than the upper major bracket, or major threshold underflow, if less than the lower major bracket. If the current statistic is outside the major bracket, an alert is added to the console, block 708, indicating the major threshold violation, but because the source of the problem is unknown, there are no changes made to the attacker database and the envelope is null. If the major bracket passes, the minor bracket is checked in the same way, block 710. Otherwise, the minor bracket check is skipped. If the current statistic is outside the minor bracket, an alert is added to the console, block 712, reporting the minor threshold violation. Once again, the source is unknown so the envelope is null.

If either a major or minor threshold violation occurs and an alert is added to the console, the next prediction is calculated at block 726, which is further described below. If there are no major or minor threshold violations, meaning the last prediction made is correct, the RTC is increased at block 716. This makes the prediction value more resistive to change as predictions become more accurate. An accurate prediction over a long period of time has a high RTC and refuses to change the value at all until the RTC is lowered sufficiently (in block 748). In block 718, the STR is increased on a successful prediction by a percentage of the short-term predictability. For example, in a system with analysis every hour, the STR can increase more than twenty-four points in a day, if the number of successful predictions in a row is high. A predictability value is increased at block 720. If the RTC is sufficiently low (a static value), the actual value from the statistics may be archived, block 722.

At block 724, the trend of the prediction is calculated. This is not the trend of the data curve but the trend of the prediction, which is called the predictability and measures the ability of the system to track a specific data curve. This is tracked using two values, one indicating how many consecutive times the prediction has been correct or incorrect, measuring the ability of the current settings to predict the data, and the percentage the prediction is correct overall (i.e., the long-term predictability of the data). The combination of these two values is the predictability of the data. If particular data points never stabilize, they can be dropped. If they were previously predictable, an analysis routine may be run to adjust the number of zones, the target percentages for the three tiers, the time ranges, and the sample size of historic data (these parameters will be better understood by referring to the discussion below beginning with block 726). Each time a single variable is changed, the new parameters are retroactively applied, and the results data is scored based on its accuracy with the actual data. The highest scoring set of parameters can be instated on the next prediction. This external routine is typically only run when short-term predictability is unstable for a data curve with a high long-term predictability.

Beginning at block 726, a new prediction is calculated following either block 708, 712, or 724, as shown in FIG. 7. At block 726, a distribution over time is calculated as follows. First, a range is found providing the values to use. Multiple predictions may be made for a single data curve breaking it into ranges of time. The minor and maximum historic values are calculated, giving the upper and lower extents of the value. By subtracting the lower extent from the upper extent, the result is the range over which the data curve varies. This range is divided into an equal number of zones starting at the lower extent and extending to the upper extent. The number of zones may vary, but is typically at least 10 and less than 20. The distribution of the actual previous samples, from the historic data, over the zones is calculated, and a target percentage is selected. The target value comes from the curve's predictability, or is 10%, for example, if there is no historic data. The bracket is adjusted based on distribution by dropping upper and lower zones that do not contain more than the target percentage of data, and the zones are recalculated with the new extents. This continues until the target is achieved or the process fails.

At block 728, a tier one bracket is calculated. The tier one bracket is wide with a target of 10%. If the data conforms to the tier one bracket, block 730, (that is, 90% of the curve hits a single zone), the prediction is set for the median of the final extents. If tier one is achieved at the 10% target, then the new prediction is added to the database and the old prediction is archived, and a tier two bracket is calculated, block 732. If the data does not conform to the tier one bracket, then the prediction fails, block 742. The predictability trend values are adjusted downward, block 744. The number of consecutive successful predictions in a row is set to −1 to indicate the trend is one failed prediction. Long term predictability is recalculated. The STR is decreased, block 746, by a percentage of the short-term predictability. The RTC is decreased, block 748, but only by a small amount. Once all thresholds are checked and adapted to current network behaviors, alert correlation begins (FIG. 8).

If a tier two bracket is calculated, block 732 the tier two bracket is slightly smaller, for example, with a target of 6%. If the data conforms to the tier two bracket (that is, 94% of the curve hits a single zone), block 734, the prediction is set for the median of the final extents. If tier two can be achieved at the 6% target, the new prediction is added to the database and the old prediction is archived, and a tier three bracket is calculated, block 736. At block 740, the tier one prediction is used if the tier two comparison fails (i.e., the data was not predictable enough to hit the 6% target) at block 734.

The tier three bracket is very narrow and is targeted at, for example, 3%. A tier three bracket is calculated, block 736. If the data conforms to the tier three bracket (that is, 97% of the curve hits a single zone), block 738, the prediction is set for the median of the final extents. If tier three can be achieved at the 3% target, then the new prediction is added to the database and old prediction is archived. At block 740, the tier two prediction is used if the tier three comparison fails (i.e., the data was not predictable enough to hit the 3% target) at block 738. The tier three prediction is used at block 740 is the tier three comparison was successful. As the prediction is compared to each of the brackets, the prediction data value or point is the same, only the allowable offset changes. The prediction is stored as the value, the offsets, the target value, the zone size, number of zones, and so on (i.e., everything necessary to calculate the next prediction). Once all thresholds are checked and adapted to current network behaviors, alert correlation begins (FIG. 8).

Figure 8:
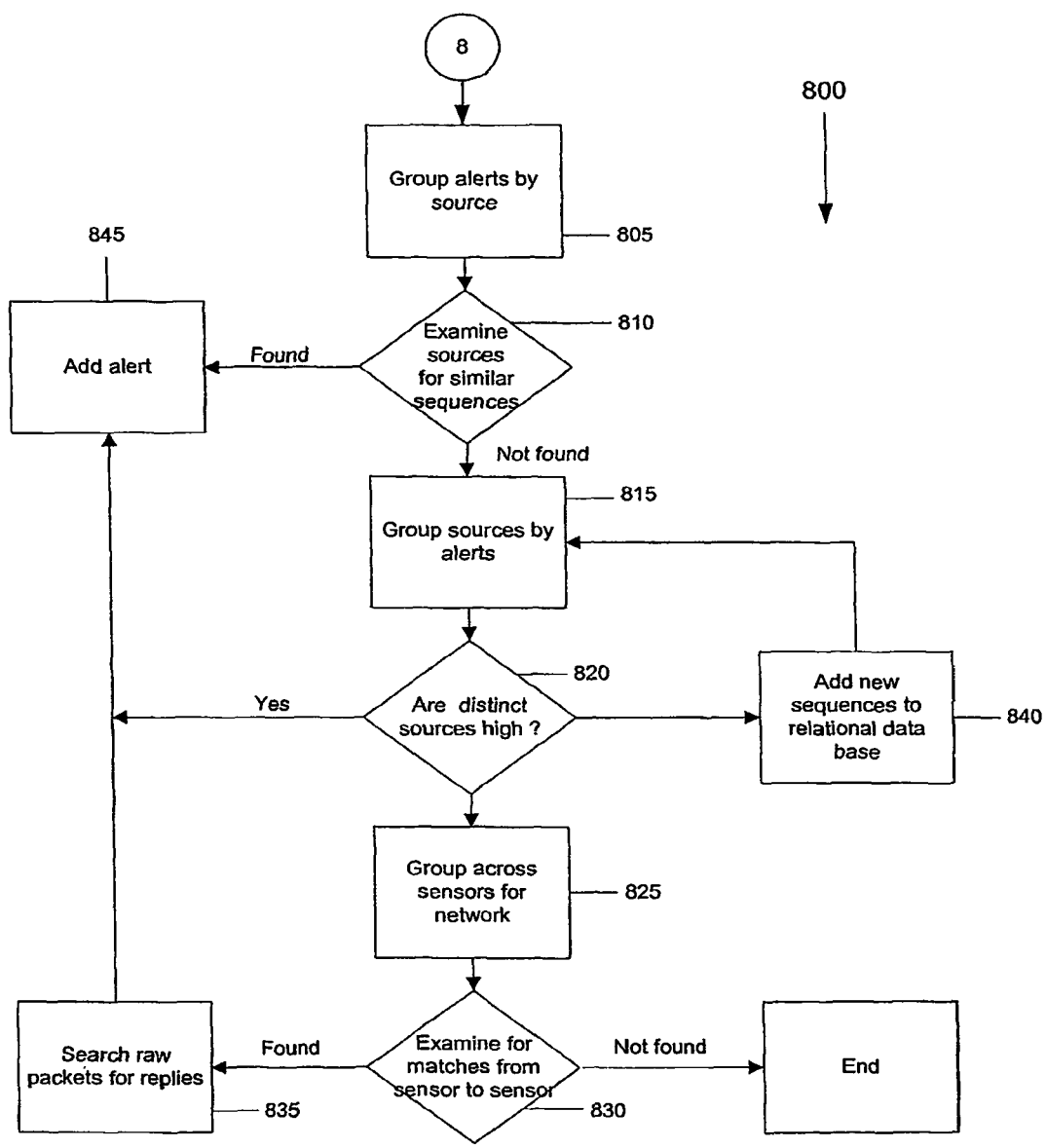
FIG. 8 shows process flow for an embodiment of alert correlation according to systems and methods of the present disclosure.

FIG. 8 shows process flow for an embodiment of alert correlation 800 according to systems and methods of the present disclosure. At this stage of behavioral analysis, all raw data has been analyzed. Alert correlation examines all alerts for the sensor to find recognizable patterns that may be used to further classify alerts. Once correlation has been performed for the sensor, correlation is performed across all sensors on the protected network. Alerts are grouped by source, block 805, so they may be easily examined. At block 810, if known sequences of alerts are found, additional alerts are generated, block 845, to further classify the attack. For example, eleven IIS:CMD.EXE alerts, three IIS:UNICODE2 alerts, and two IIS:UNICODE2 alerts all from the same source in a specific order is a Nimda worm attack. The additional alert generated is WORM:NIMDA.

The sources are grouped by alert type, block 815. This shows a count of distinct sources for each type of alert. At block 820, it is determined whether there is a high number of distinct sources. The higher the distinct count of sources for each alert, the more active the event (associated with the alert) is on the network. This information may also be used to adjust the technique discriminators used in block 545 (see FIG. 5) and to note new attack trends. If there is a high number of distinct sources, an alert is added, block 845. Any new sequences found are added to the relational database, block 840, and the process returns to block 815. Following analysis at block 820, alert correlation proceeds to block 825, network correlation. Network correlation looks for the same alerts on multiple sensors on the protected network. Alerts from related sensors are pooled into a single alert pool (logically, but not necessarily physically).

At block 830, an examination for matches from sensor to sensor is performed. The direction of each alert is known. An alert moving from an external sensor to an internal sensor should first hit the external system then the internal system. When an alert on an external sensor has a matching alert of the same source (within an appropriate time frame) on an internal sensor, it indicates the network has been penetrated (vice versa for an outgoing attack). If no matches are found, alert correlation ends. If matches are found, the raw packets are searched, block 835, for a reply indicating the attack worked. If so, the alerts are escalated to a high priority. Block 845 is a standard add alerts, and because the sources are known, the attacker's SIR is increased.

Figure 9:
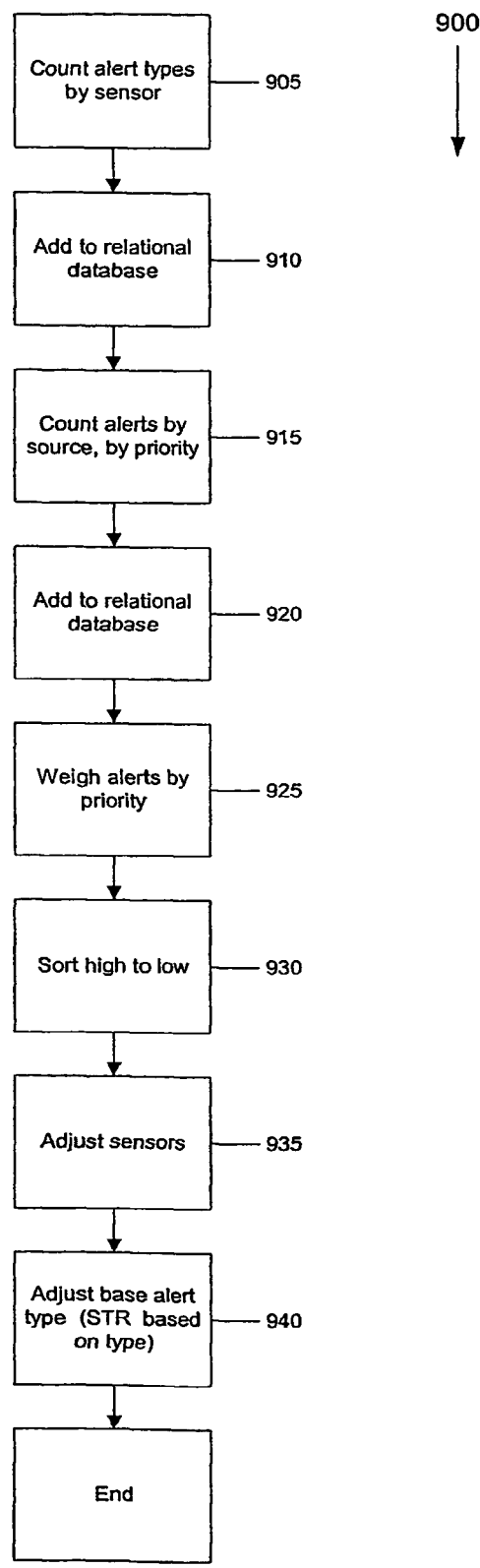
FIG. 9 shows process flow for an embodiment of global analysis according to systems and methods of the present disclosure.

A global analysis may be performed including analysis of all available sensors across multiple networks. FIG. 9 shows process flow for an embodiment of global analysis 900 according to systems and methods of the present disclosure. Global analysis is designed to analyze attack sources from the Internet across the whole customer profile. By performing this analysis, scanning or attack sources can be identified across subnets or across the Internet. Additionally, if coordinated attacks are occurring and are being performed against multiple sites, they can be found using global analysis. As the number of data sources increases, the quality of this analysis improves.

Global analysis may be used to analyze thousands or even hundreds of thousands of sources across the Internet at a central site in an attempt to find sources of suspicious activity. Attackers can perform vulnerability scans on many targets at once, and often do so in an attempt to hide the attack. Instead of scanning one target for 500 different vulnerabilities at once, they may scan 200 sites for the same vulnerabilities. The attacker's computer may be busy twenty-four hours a day, but each site receives a tiny portion of scan each day and therefore manages to stay under the rate that is detectable by traditional knowledge-based systems.

Referring now to the exemplary global analysis shown in FIG. 9, alerts are counted by alert type for sources outside the protected networks of the sensors at block 905. This yields alert frequencies by type, which indicate attack methods being used. At block 910, alert counts are added to the RDB. Alerts are then counted by source and priority, block 915, showing which attackers are most active on the global network. At block 920, attacker information from block 915 is added to the RDB. Global alerts are weighted by priority, block 925. Higher priority alerts are given additional counts in both alert type tables and attacker tables.

At block 930, in a first table, a set of alerts with a weighted count representing the type of alerts on the global network is created. In a second table, global attack sources are also weighted by priority, with both tables being sorted from high to low. Sensors are adjusted, block 935. Attacker source strengths are raised in sensor attacker databases so alert SSVs from the same sources are automatically higher. Alert type default priorities may be adjusted, block 940, based on the global alert frequencies. These can be pushed to either default priorities of alerts or to the static technique discriminators (preferred). Once global analysis is complete, the results are sent to each sensor for each protected network analyzed as part of the global analysis (see block 950, FIG. 2).

Figure 10:
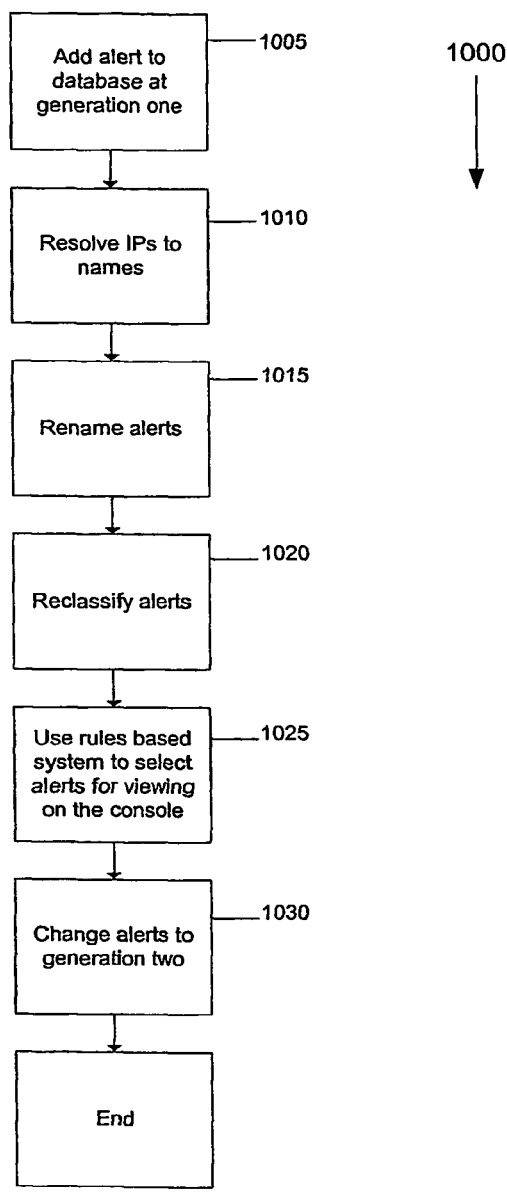
FIG. 10 shows process flow for an embodiment of alert release system according to systems and methods of the present disclosure.

Optionally, systems and methods of intrusion detection according to the present disclosure may include an alert release system to assist operators of the IDS. Process flow for an embodiment of an alert release system is shown in FIG. 10. This system is designed to reduce the number of alerts an operator of the IDS has to view while maintaining a larger number of alerts for correlation and analysis. Alerts are created in a generational system, and higher generation alerts are shown on the operator on the console. Alerts are selected for display by a series of rules that define the alerts that should be displayed. The series of rules are generally high level selection parameters, but may be used to selectively show or ignore alerts based on very specific criteria, such as, for example, ignoring all alerts from a particular source or ignoring all alerts in a particular time window.

The series of rules may be applied in a specific order such that once a single rule is applied resulting in an indication that the alert should not be displayed, fer rules no longer need to be applied to that alert and the alert is not displayed. Additionally, all rules may be applied to an alert and the alert may be displayed only if a certain percentage of the rules indicated that the alert should be release to the console. For example, if ten rules are present, the system may be set up to release an alert if seven or more rules indicate that the alert should be released. Furthermore, the rules could be weighted such that the indication based on a certain (possibly, more reliable) rule is weighted heavier than the indication based on another rule. Accordingly, only alerts of a specific significance are displayed on the console.

The series of rules or selection rules may contain alert fields such as source, destination, source port, and destination port in addition to other critical pieces of information from behavioral analysis. SSV is a strong indicator of activity on a network. Additionally, the number of alerts of a specific type and/or the frequency of alerts may indicate the alert should be released.

Maintaining alerts in an intermediate storage area that is not automatically displayed to the operator of the IDS allows additional processing to be performed on alerts before they are displayed. Another correlation pass could be performed to reclassify alerts not yet released. By looking for sequence indicators, multiple alerts may be combined into single alerts and only the single alert is displayed. To reclassify alerts, alerts in sequence that correlate to a known type of attack are not released, but rather a new alert is generated and released.

As an example of the functionality alert release system, consider the Nimda worm. Five alerts are used to determine that a web attack is actually a Nimda worm attack. The five alerts are not released to the console, instead a new alert called Nimda is generated and this new alert is released to the console. This preserves the record that five attacks occurred but that they were all from the same source (as with a Nimda worm attack).

An alert release system also allows sources and services to be renamed, providing name resolution for alerts so that servers (including internal servers where no public DNS is available) may be renamed. A table resolves addresses to names. For example, before alerts are released to the console, the addresses are changed to meaningful names, such as "firewall." The operator of the IDS sees the name rather than the address, which is beneficial because the human operator is more likely to immediately recognize the name. Address information is maintained in the alert for the operator's use and reference.

Additionally, alerts may be renamed after alerts have been generated and imported from a signature-based server using this alert release system. Previously, all importers maintained a list of alert names that needed to changed at the time of import, each of which were unique to the signature-based system generating the alerts. The alert release system allows a single list of alert renames to be used to change all alerts of a particular name to another name to assure unified data names.

Referring now to FIG. 10, where an exemplary process flow for an embodiment of an alert release system according to systems and methods of the present disclosure is shown, at block 1005, alerts are added to a database at generation one. IP addresses are resolved to names, block 1010, and alerts are renamed, block 1015. Alerts are reclassified, block 1020, and a series of selection rules are used to select alerts that are to be displayed on the console, block 1025, for viewing by the operator of the IDS. The alerts selected for display are assigned generation two status, block 1030, and stored in a generation two alert database.

The foregoing description of exemplary embodiments according to systems and methods of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

I claim:

1. A method, comprising:
performing, using one or more computer systems:
identifying normal behavior in a network based, at least in part, upon network traffic sampled over a period of time;
receiving packets transmitted through the network;
selecting a portion of the received packets that does not display the normal behavior based, at least in part, upon a comparison between the received packets and the normal behavior;
rating the selected packets, at least in part, according to their deviations from the normal behavior;
generating an alert in response to one or more of the selected packets having a rating that meets a threshold value, the alert having a strength assigned thereto, the strength associated with the alert's abnormality;
receiving a human-assigned score associated with the alert, the score being reflective of a prediction accuracy;
combining the strength and the score associated with the alert into a strength-score value; and
determining whether to escalate the alert as a function of the strength-score value.

2. The method of claim 1, wherein the network includes disparate sources, and wherein the disparate sources include at least one server and at least one firewall.

3. The method of claim 1, wherein the period of time is sufficient to yield a statistically significant sample of historical traffic data.

4. The method of claim 1, wherein identifying the normal behavior includes determining one or more sequences of behavioral patterns, each sequence including a series of network events ordered in time.

5. The method of claim 1, wherein identifying the normal behavior includes determining one or more thresholds of behavioral patterns, each of the one or more thresholds of behavioral patterns including a number of network events.

6. The method of claim 1, wherein selecting the portion of the received packets that do not display the normal behavior includes excluding those among the received packets that display the normal behavior.

7. The method of claim 1, wherein rating the selected packets includes scoring the selected packets independently of one or more criteria used in the selection.

8. The method of claim 1, wherein rating the selected packets further comprises:
grouping the selected packets into sets of packets, each packet within a given set of packets having a characteristic in common with other packets of the same set of packets;
comparing each of the sets of packets against the normal behavior; and
scoring each packet within a given set of packets according to the given set of packet's deviation from the normal behavior.

9. The method of claim 8, wherein the characteristic includes at least one of: a source port, a destination port, a source address, a destination address, or a protocol.

10. The method of claim 8, wherein scoring each packet includes generating statistics configured to correlate two or more of the sets of packets.

11. The method of claim 1, wherein generating the alert further comprises:
performing, using the one or more computer systems:
identifying a source associated with the alert; and
applying a Resistance-to-Change (RTC) bias to the rating, the RTC bias associated with the source and configured to reduce a magnitude of the rating.

12. The method of claim 1, further comprising:
performing, using the one or more computer systems:
updating the normal behavior based, at least in part, upon the alert.

13. The method of claim 1, further comprising:
performing the identifying, receiving, selecting, rating, and generating operations across a plurality of networks; and
compiling results in a global database.

14. A tangible non-transitory computer storage medium having program instructions stored thereon that, upon execution by a processor within a computer system, cause the computer system to:
receive packets transmitted through a network;
exclude, from the received packets, packets that display a normal behavior based, at least in part, upon a comparison between the received packets and the normal behavior;
rate remaining ones of the received packets as a function of their deviations from the normal behavior;
generate an alert in response to one or more of the remaining packets having a rating that meets a threshold value;
identify a source associated with the alert; and
apply a Resistance-to-Change (RTC) bias to the rating, the RTC bias associated with the source and configured to reduce a magnitude of the rating.

15. The non-transitory computer storage medium of claim 14, wherein the normal behavior is identified based, at least in part, upon network traffic sampled over a period of time sufficient to yield a statistically significant sample of historical traffic data.

16. The non-transitory computer storage medium of claim 15, wherein the normal behavior includes at least one of: (a) one or more sequences of behavioral patterns, each sequence including a series of network events ordered in time, or (b) one or more thresholds of behavioral patterns, each threshold including a number of network events.

17. The non-transitory computer storage medium of claim 16, wherein the receive, exclude, rate, generate, identify, and apply occur across a plurality of networks, and wherein the program instructions, upon execution, further cause the computer system to:
compile results in a global database; and
update historical data based on the results from the global database.

18. A system, comprising:
a processor; and
a memory coupled to the processor, the memory configured to store program instructions executable by the processor to cause the system to:
receive packets transmitted through a network;
eliminate packets that display a normal behavior based, at least in part, upon a comparison between the packets and the normal behavior;
generate an alert in response to one or more remaining packets having a rating that meets a threshold value;
apply a Resistance-to-Change (RTC) bias to the rating, the RTC bias associated with a source corresponding to the alert and configured to reduce a magnitude of the rating;
assign a strength to the alert, the strength associated with the alert's abnormality;
receive a human-assigned score associated with the alert, the score being reflective of a prediction accuracy;
combine the strength and the score associated with the alert into a strength-score value; and
determine whether to escalate the alert as a function of the strength-score value.

19. The system of claim 18, wherein the program instructions are executable by the processor to further cause the system to:
group the remaining packets into sets of packets, each packet within a given set of packets having a characteristic in common with other packets of the same set of packets, the characteristic including at least one of: a source port, a destination port, a source address, a destination address, or a protocol;
compare each of the sets of packets against the normal behavior; and
rate each packet within a given set of packets according to the given set of packet's deviation from the normal behavior.

20. The system of claim 18, wherein the receive, eliminate, generate, apply, assign, receive, combine, and determine occur across a plurality of networks, and wherein the program instructions are executable by the processor to further cause the system to:
compile results in a global database; and
update historical data based on the results in the global database.

* * * * *